United States Patent [19]
Betz et al.

[11] 3,997,837
[45] Dec. 14, 1976

[54] GAS ANALYSIS DEVICE

[75] Inventors: Gregor Betz, Dusseldorf; Hugo-Peter Scholz, Essen, both of Germany

[73] Assignee: Fried. Krupp Gesellschaft mit beschrankter Haftung, Essen, Germany

[22] Filed: Feb. 20, 1975

[21] Appl. No.: 551,324

[30] Foreign Application Priority Data

Feb. 21, 1974 Germany .......................... 2408218

[52] U.S. Cl. ..................... 324/71 SN; 340/237 R; 338/34; 73/27 R
[51] Int. Cl.² ........................................ G01N 27/14
[58] Field of Search ............ 324/71 SN, 65, 140 R; 73/27; 338/34; 340/237 R

[56] References Cited
UNITED STATES PATENTS

| | | |
|---|---|---|
| 3,051,895 | 8/1962 | Carson ................................ 324/71 |
| 3,392,333 | 7/1968 | Blondfield ......................... 324/140 |
| 3,678,489 | 7/1972 | Scherban ......................... 340/237 R |
| 3,733,595 | 5/1973 | Benedict ......................... 340/237 R |
| 3,739,260 | 6/1973 | Schadler ............................. 324/33 |
| 3,754,219 | 8/1973 | Klein ............................. 340/237 R |
| 3,778,229 | 12/1973 | Webster et al. .................. 23/254 E |
| 3,859,644 | 1/1975 | Main ............................... 340/228 R |
| 3,887,335 | 6/1975 | Boutonnat ........................ 23/254 E |

Primary Examiner—Robert Segal
Assistant Examiner—Vincent J. Sunderdick
Attorney, Agent, or Firm—Spencer & Kaye

[57] ABSTRACT

In a system for analyzing a gas mixture and including a semiconductor gas measuring sensor and an indicating element, a differential amplifier is connected in series between the sensor and the indicating element.

16 Claims, 6 Drawing Figures

FIG.1a
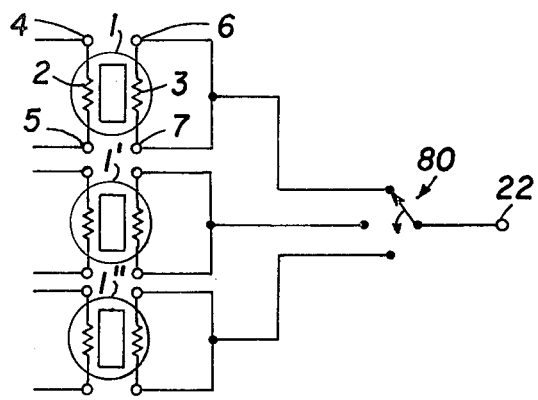
FIG.2
FIG.3
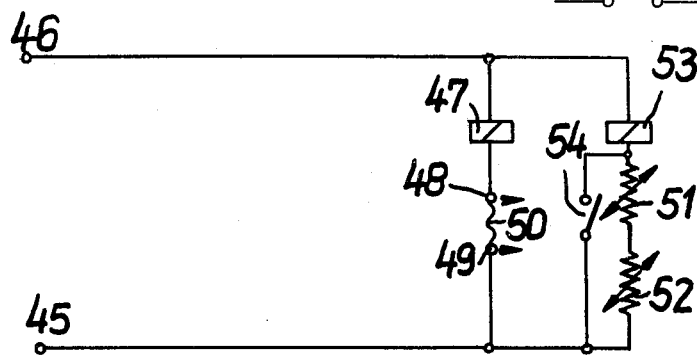
FIG.5
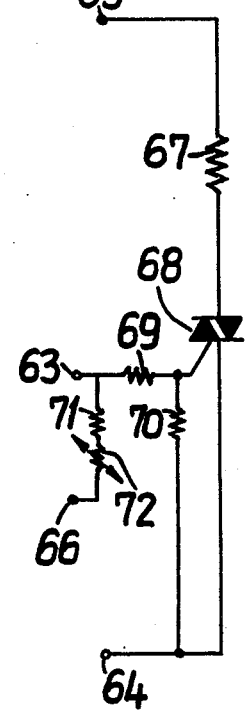
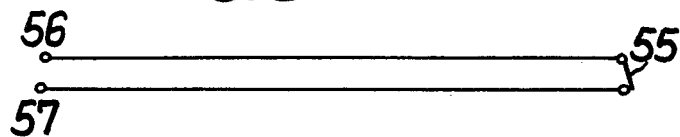
FIG.4
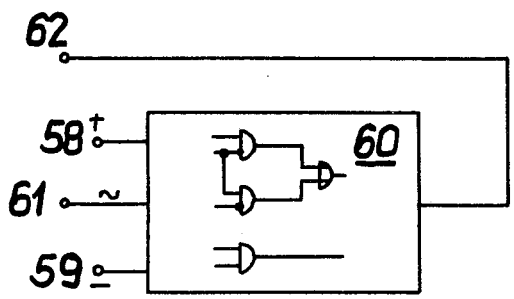

GAS ANALYSIS DEVICE

BACKGROUND OF THE INVENTION

The present invention relates to a device for the qualitative and quantitative analysis of gas mixtures, employing semiconductors as the measuring sensors.

It is known that the electrical properties of certain semiconductors vary when they come in contact with gases, e.g., hydrogen, carbon monoxide, methane, propane and ethanol, and it is possible to utilize such semiconductors for gas analyses. The drawback in the known gas analyzers is that they have a complicated structure, are very large and heavy, require frequent maintenance and involve high investment costs.

SUMMARY OF THE INVENTION

It is an object of the present invention to provide a gas analyzer which is equipped with semiconductor measuring sensors and which requires little maintenance, has small dimensions and low weight, is movable, can be used outside of chemical laboratories and is sufficiently accurate.

These and other objects according to the invention are achieved by connecting one or a plurality of measuring sensors to an electronic differential amplifier which is connected in series selectively with one or more light emitting diodes and/or measuring and recording devices, or pulse switches.

For mobile use of the gas analyzer according to the invention it is advantageous to provide both d.c. and a.c. voltage from a battery, the alternating voltage being produced by an inverter.

If a plurality of measuring locations are to be interrogated, according to a further embodiment of the invention, the measuring sensors are automatically and sequentially connected to the electronic differential amplifier by means of a switching circuit.

In continuous processes involving the generation of gases which are to be monitored, it is particularly advantageous if the time and duration of the measurements are controlled by the process being monitored. Processes which produce, during their starting and ending phases, gas mixtures differing in composition from the gas mixtures produced during normal operation can be monitored particularly well according to the present invention if there is provided a time relay which switches the device on only after the process to be monitored has completed its starting phase and switches it off before the ending phase. However, in many cases it may be advantageous if the device is provided with an electric counter which interrupts the measurements in the process being monitored, in which many identical individual processes take place in succession, only when at least one starting phase, one normal phase and one ending phase of an individual process have been covered. The possibilities of use of such a device are expanded since its sensitivity and the reaction limits of the electronic differential amplifier are automatically adapted to the operating conditions by variable resistances.

For economical processing of the measuring results, it is often appropriate for the electrical signals from several of the measuring sensors, after being amplified in the electronic differential amplifier or amplifiers, to appear as a common output signal.

According to a further embodiment of the invention, the device is provided with a coding and decoding unit which switches the device on and off at certain times. The accuracy, speed and stability of a device according to the present invention are particularly improved when the electronic differential amplifier is provided with a contactless electronic power switch which switches the electrical load and when the electronic differential amplifier has a feedback connection between its output to its non-inverting input, the coupling members in this feedback including one or a plurality of resistors. The electronic differential amplifier together with its input circuit are tuned so that different electrical potentials appear between the amplifier output and the positive pole of the direct current source when different operating states exist, these potentials being unequal to zero.

If the device according to the present invention also performs a process control function, it is advantageous for the device to be provided with a time relay which is controlled by the amplifier and which switches off the process after a time delay which is sufficient to regulate the process. If measuring data of several devices are to be gathered and evaluated in a central data processing system, the device according to the invention will be designed so that it is connected in series with a carrier frequency signal generating device which adapts the signals for long-distance transmission by way of frequency modulation and/or amplitude modulation.

The gas analyzer according to the invention has particular advantage, compared to the prior art, that it has sufficient measuring accuracy and a low initial cost and can be emloyed directly at the location where the gas mixtures are produced. The gas analyzer is particularly suitable for monitoring the exhaust gases of furnace systems, for monitoring the air in air-conditioned rooms and for controlling air-conditioning systems, for the continuous monitoring of air pollution, for measuring the alcohol content in the human breath, and the like.

BRIEF DESCRIPTION OF THE DRAWING

FIG. 1a is a circuit diagram of a modified version of a portion of the circuit of FIG. 1.

FIG. 2 is a circuit diagram of a switch-on device for the gas analyzer.

FIG. 3 shows an embodiment of a switch-on device for a gas conveyor connected ahead of the gas analyzer.

FIG. 4 is a circuit diagram of a coding and decoding device which may be combined with the switch-on device of FIG. 2.

FIG. 5 is a circuit diagram of a contactless electronic power switch for the circuit of FIG. 1.

DESCRIPTION OF THE PREFERRED EMBODIMENTS

Figure 1:
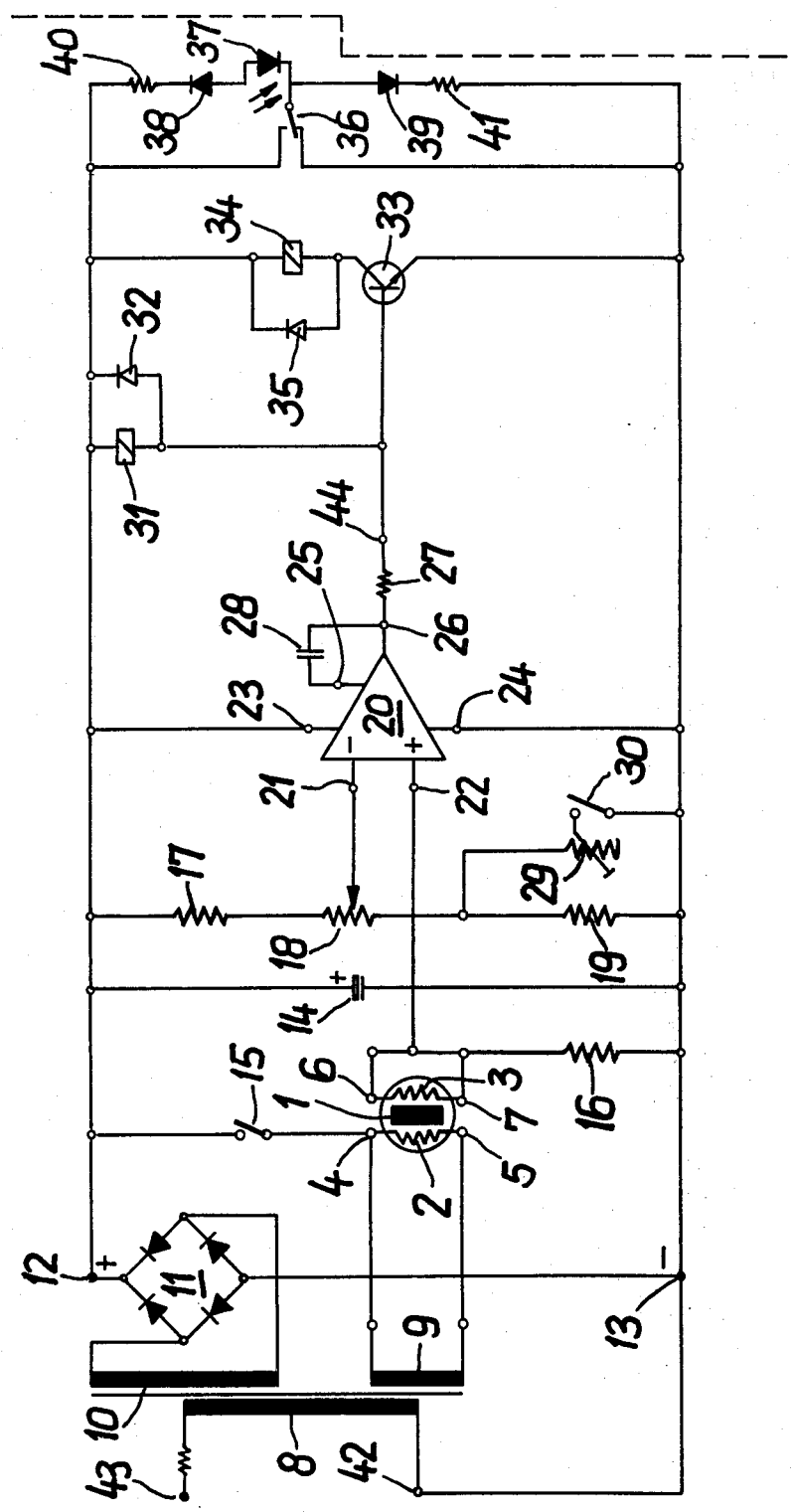
FIG. 1 is a circuit diagram of one embodiment of a gas analyzing device according to the invention.

FIG. 1 shows a device according to the present invention for the analysis of gas. A semiconductor which is suitable for operation as measuring sensor 1 is disposed in a measuring chamber (not shown) to allow it to be brought into contact with the gas to be analyzed. The semiconductor is sensitized for a certain type of gas, for example carbon monoxide, and emits, when it comes in contact with carbon monoxide, an electrical signal which varies in magnitude in proportion to the carbon monoxide concentration. A silicon semiconductor containing a small amount of boron is used, for example, as a measuring sensor for identifying the carbon monoxide.

The measuring chamber can also accommodate a plurality of semiconductors which are suited as measuring sensors 1.

The measuring sensor 1 is provided with two pairs of electrodes 2 and 3 with one or the other pair being heated. The pairs of electrodes 2 and 3 are supplied with voltage via the secondary windings 9 and 10 of transformer 8 and a full wave rectifier 11 across which a filter capacitor 14 is connected. Rectifier 11 and capacitor 14 thus constitute a direct current source.

The pair of electrodes 2 is connected with the secondary winding 9 via terminals 4 and 5 and the current flowing between electrodes 2 heats the measuring sensor 1. The operating temperature of the measuring sensor 1, depends on the composition of the gas mixture to be analyzed and is between 80° and 120° C. The pair of electrodes 2 is connected with the positive terminal 12 of the direct current source via relay contact 15 and terminal 4.

The pair of electrodes 3 is connected, via terminals 6 and 7 and resistor 16, with the negative terminal 13 of the direct current source and, via terminals 6 and 7, with the positive input terminal 22 to the non-inverting input of the electronic differential amplifier 20.

Resistors 17, 18 and 19 form a voltage divider which determines the amplification factor of amplifier 20. The desired potential, or rated value, for point 21 of the inverting input of the electronic differential amplifier 20 can be obtained by proper setting of the slider of potentiometer 18.

The electronic differential amplifier 20 is supplied with the necessary operating voltage via terminals 23 and 24 while the amplified output signals can be obtained between terminal 26 and the positive terminal 12 of the direct current source. The electronic differential amplifier 20 is connected with capacitor 28 via terminals 25 and 26 and is frequency-compensated thereby. An integrating circuit designated "TAA 861" or "TAA 761" and manufactured by Siemens AG, Munich, Federal Republic of Germany, is used, for example, as an electronic differential amplifier 20.

The amplifier output signals from the electronic differential amplifier 20 are applied to output terminal 44 via a resistor 27 to act on a relay 34 via a relay 31 and a driver stage 33 so that the switch 36 of a gallium-arsenide diode 37 is actuated. The relays 31 and 34 are stabilized by attenuation diodes 32 and 35, respectively.

The relay 31 controls direct the subsequent regulating and alarm devices, whereas the relay 34 controls the subsequent indicating elements. The output of the amplifier 20 is not sufficient to directly actuate the two relays 31 and 34 simultaneously. Therefore, the relay 31 is actuated directly from the amplifier 20 and the relay 34 is actuated indirectly via the driver stage 33 which receives a low energy input.

A variable resistor 29 is arranged so that it is connected in parallel with resistor 19 by closed switch 30. Switch 30 is opened and closed by a relay, e.g., relay 53 of FIG. 2. Resistor 29 is adjusted to reduce the sensitivity of the electronic amplifier 20 to the extent that it will not switch through under certain conditions, as for example during the starting period of an oil burner.

If the transformer 8 receives an alternating supply voltage on its primary side, applied between terminals 43 and 42, the gas analyzer is supplied with alternating and direct current through the two secondary windings 9 and 10 and full wave rectifier 11. Closing of relay contact 15 enables the system to take measurements and the potential between the positive terminal 22 and the negative terminal 21 is regulated by voltage divider 17, 18, 19 so that the amplifier will not respond at a potential value below the rated value for the gas concentration but will switch through, i.e., produce an amplified output, at a value which lies above the rated value. Relay 31 then switches through visible or audible signals, emits control pulses if desired or switches off the process being monitored, for example the combustion of oil.

During normal operation of the gas analyzer, relay 34 is actuated to move switch 36 in the direction to connect the gallium-arsenide diode 37 to the negative side 13 of the direct current supply, and when a certain gas concentration is being exceeded, it moves switch 36 to connect diode 37 to the positive side 12. Depending on the operating state indicated by the state of relay 34, the gallium-arsenide diode 37 emits red or green light since the break-point voltage of diodes 38 and 39 is set correspondingly via voltage divider 40, 41.

FIG. 1a shows a modified arrangement where three measuring sensors 1, 1' and 1'' are provided for permitting a plurality of measuring locations to be interrogated. The pair of electrodes 3 of each sensor is connected to a respective contact of a switch 80 whose movable contact is connected to the positive input 22 of amplifier 20 so that operation of switch 80 enables the several sensors to be automatically and sequentially connected to amplifier input 22.

FIG. 2 shows a switch-on device for the gas analyzer and an arrangement for varying its sensitivity. Terminals 45 and 46, for example, are connected to the automatic oil combustion system of such a burner. If a process is started in which there are formed gas mixtures whose compositions are to be monitored, terminals 45 and 46 receive a switching voltage. Relay 47 also receives a voltage via terminals 48 and 49 which are connected by a jumper 50. It is desirable for the jumper 50 to be of the plug-in (exchangeable) type.

Relay 47 is provided to close relay contact 15 of FIG. 1 and switch 55 of FIG. 3. Thus the gas analyzer is ready to take measurements and the supply of gas to the measuring sensor 1 is started.

Resistors 51 and 52 have a negative temperature coefficient and their values are selected so that relay 53 will not be initially actuated by the voltage present between terminals 45 and 46. After a settable period of time the two resistors 51 and 52 are heated to such an extent that the passage of current is sufficient to actuate relay 53. Then switch 54 is closed to protect resistors 51 and 52 against overheating. Moreover, relay 53 is associated with switch 30 of FIG. 1 so that switch 30 is opened upon actuation of relay 53. This increases the sensitivity of the electronic differential amplifier 20, which had been reduced during the starting phase of the process. The delay produced by the heating of resistors 51 and 52 is adjusted so that it corresponds to the starting phase of the process to be monitored.

FIG. 3 shows a switch-on device for the gas supply device connected ahead of the gas analyzer. When relay 47 closes switch 55, gas is conveyed to measuring sensor 1. Terminals 56 and 57 are connected in series between a power source and a gas conveying pump.

FIG. 4 shows a coding and decoding device which can be combined with the switch-on device of FIG. 2. If the jumper 50 is removed and terminals 48 and 49 are connected with terminals 58 and 59 of the coding and decoding device 60, the coding and decoding device 60 will switch on the relay 47, and thus the measuring process, only after completion of an arbitrarily settable number of processes in which the gas mixture to be analyzed is produced. In this way it is possible to monitor, for example, every tenth combustion process in an oil burner. The coding and decoding device 60 may be replaced by a timer. Alternatively, the coding and decoding device 60 and timer switches may be connected in series between 48 and 49, respectively.

The coding and decoding device 60 used is a slow noiseproof logic module which can be coded via its set-input and actuates the relay 47 by network counting or by counting the burner switch-on impulses at the pre-selected time or on reaching the pre-selected impulse rate.

FIG. 5 shows a contactless electronic power switch which may replace the load switch which is more commonly employed and which is constituted by relay 31 in the embodiment shown in FIG. 1. If the contactless electronic power switch is used, the relay 31 and diode 32 shown in FIG. 1 are not required and the output terminal 44 of the differential amplifier is connected with terminal 63, terminal 42 is connected with terminal 64, terminal 65 is connected with terminal 43 and terminal 66 is connected with terminal 21 of the inverting input of the electronic differential amplifier 20.

The load 67 is switched by a contactless power switch 68, for example a triac, which is controlled, via resistors 69 and 70 which act as voltage dividers, by the output at terminal 44 of the differential amplifier and via terminal 63. The fixed resestance 71 and the variable resistance 72 produce a feedback connection via terminal 66 and the inverting input 21 of the electronic differential amplifier 20 which stabilized the control of the contactless power switch 68.

It will be understood that the above description of the present invention is susceptible to various modifications, changes and adaptations, and the same are intended to be comprehended within the meaning and range of equivalents of the appended claims.

We claim:

1. In a system for analyzing a gas mixture, the system including a semiconductor gas measuring sensor, the improvement wherein said system comprises: a source of reference voltage; a differential amplifier having a non-inverting signal input and an inverting signal input, one of said inputs being connected to the output of said measuring sensor, and the other of said inputs being connected to said reference voltage source, said amplifier further having an output at which appears a voltage proportional to the difference between the voltages at its signal inputs and representative of the signal appearing at the output of said measuring sensor; indicating means; and circuit means connecting said output of said amplifier to said indicating means for causing said indicating means to produce an indication when the voltage of said output of said amplifier exceeds a selected value.

2. A system as defined in claim 1 wherein said indicating means comprises a light emitting diode.

3. A system as defined in claim 1 wherein said measuring sensor comprises a semiconductor base and two pairs of electrodes disposed on said semiconductor base, each of said electrode pairs being provided with two external connection terminals, and further comprising power supply means including a d.c. voltage supply, and an a.c. voltage supply; means connecting said power supply means to one of said pairs of electrodes; and means connecting the terminals of the other of said pairs of electrodes together at a common point constituting said output of said sensor.

4. A system as defined in claim 1 wherein there are a plurality of semiconductor gas measuring sensors and said system further comprises switch means connected between said sensors and said one amplifier input for automatically connecting each sensor to said one amplifier input in sequence.

5. A system as defined in claim 1 wherein the gas mixture to be analyzed is produced in the course of a process, said system further comprising operation control means connected for controlling the moment and duration of an analysis operation in response to a parameter of such process.

6. A system as defined in claim 5 wherein said operation control means comprises time delay means connected for initiating an analyzing operation after completion of the starting phase of such process and for terminating such analyzing operation prior to commencement of the end phase of such process.

7. A system as defined in claim 5 wherein the gas mixture to be analyzed is produced in the course of a periodically recurring process, each occurrence of which includes, in sequence, a starting phase, a normal phase and an end phase, and said operation control means comprises an electronic counter connected for terminating an analyzing operation only after the starting phase, normal phase and end phase of one occurrence of such process have taken place.

8. A system as defined in claim 1 wherein said reference voltage source comprises variable resistance means, and switch means arranged for selectively connecting said variable resistance means to said other input of said differential amplifier for varying the sensitivity and response limits thereof.

9. A system as defined in claim 1 wherein there is a plurality of semiconductor gas measuring sensors connected to said one amplifier input, and wherein the voltage at said amplifier output constitutes a common output signal representative of the signals appearing at the outputs of all of said sensors.

10. A system as defined in claim 1 further comprising coding and decoding means connected for controlling the initiation and termination of gas analysis operations.

11. A system as defined in claim 1 further comprising an output load member and a contactless electronic power switch connected for supplying power to said load when the voltage at said amplifier output exceeds a selected value.

12. A system as defined in claim 1 wherein said amplifier further includes resistance means forming a feedback branch connected between said amplifier output and said inverting input.

13. A system as defined in claim 1 further comprising a source of d.c. voltage connected to said amplifier and wherein said amplifier includes input circuit means arranged to time said amplifier for causing different electrical potentials to appear between said amplifier output and the positive terminal of said voltage source upon the occurrence of different operational conditions.

14. A system as defined in claim 1 wherein the gas mixture is being produced by a process and said system further comprises time delay relay means connected to be controlled by the voltage at said amplifier output for switching off the process after a time delay sufficient to regulate such process.

15. A system as defined in claim 1 further comprising carrier frequency signal generating means connected for modulating a carrier frequency signal with signals resulting from a gas measurement for long distance transmission of the modulated signal.

16. A system as defined in claim 3 wherein said power supply means comprises a battery constituting said d.c. voltage supply and an inverter constituting said a.c. voltage supply.

* * * * *

UNITED STATES PATENT AND TRADEMARK OFFICE
CERTIFICATE OF CORRECTION

PATENT NO. : 3,997,837
DATED : December 14th, 1976
INVENTOR(S) : Gregor Betz et al It is certified that error appears in the above-identified patent and that said Letters Patent are hereby corrected as shown below:

In the heading of the patent, change the Assignee to read:
--Karl Josef Ehlen, Möhnesee-Wamel, Germany--

Signed and Sealed this

Twenty-second Day of February 1977

[SEAL]

Attest:

RUTH C. MASON
*Attesting Officer*

C. MARSHALL DANN
*Commissioner of Patents and Trademarks*